United States Patent
von Ramm et al.

(10) Patent No.: US 10,605,903 B2
(45) Date of Patent: Mar. 31, 2020

(54) PMUT ARRAY FOR ULTRASONIC IMAGING, AND RELATED APPARATUSES, SYSTEMS, AND METHODS

(71) Applicants: Olaf T. von Ramm, Efland, NC (US); John B. Castellucci, Durham, NC (US)

(72) Inventors: Olaf T. von Ramm, Efland, NC (US); John B. Castellucci, Durham, NC (US)

(73) Assignee: Duke University, Durham, NC (US)

( * ) Notice: Subject to any disclaimer, the term of this patent is extended or adjusted under 35 U.S.C. 154(b) by 855 days.

(21) Appl. No.: 14/662,000

(22) Filed: Mar. 18, 2015

(65) Prior Publication Data

US 2015/0265245 A1    Sep. 24, 2015

Related U.S. Application Data (60) Provisional application No. 61/954,750, filed on Mar. 18, 2014.

(51) Int. Cl.
| | |
|---|---|
| G01S 7/52 | (2006.01) |
| B06B 1/06 | (2006.01) |
| A61B 8/00 | (2006.01) |
| A61B 8/14 | (2006.01) |
| A61B 8/08 | (2006.01) |

(52) U.S. Cl.
CPC ........ G01S 7/52017 (2013.01); A61B 8/4494 (2013.01); B06B 1/0625 (2013.01); B06B 1/0648 (2013.01); A61B 8/0858 (2013.01); A61B 8/14 (2013.01)

(58) Field of Classification Search
None
See application file for complete search history.

(56) References Cited

U.S. PATENT DOCUMENTS

| | | |
|---|---|---|
| 6,086,539 A | 7/2000 | Guracar et al. |
| 6,430,109 B1 | 8/2002 | Khuri-Yakub et al. |
| 6,530,885 B1 | 3/2003 | Entrekin et al. |
| 7,449,821 B2 | 11/2008 | Dausch |

(Continued)

OTHER PUBLICATIONS

Choi et al., "A two-dimensional electromechanical composite plate model for piezoelectric micromachined ultrasonic transducers (pMUTs)." 2010, J. Micromech. Microeng. pp. 1-12.*

(Continued)

*Primary Examiner* — James M Kish
(74) *Attorney, Agent, or Firm* — Withrow & Terranova, P.L.L.C.

(57) ABSTRACT

Piezoelectric Micromachined Ultrasound Transducer (pMUT) arrays for ultrasonic imaging, and related apparatuses, systems, and methods are disclosed. In one embodiment, an ultrasonic imaging assembly comprises a substrate and a plurality of array elements arranged on the substrate in an array. Each array element comprises at least one pMUT disposed on the substrate each having a geometry configured to accept a predetermined fundamental mode vibration. The plurality of array elements are configured to transmit and receive at least one ultrasound beam based on the predetermined fundamental mode vibration. By sizing the pMUTs to correspond to a desired fundamental mode vibration, the pMUT array has improved sensitivity, and can be produced relatively cheaply compared to conventional dicing methods.

21 Claims, 10 Drawing Sheets

(56) References Cited

U.S. PATENT DOCUMENTS

| | | | |
|---|---|---|---|
| 2004/0133104 A1 | 7/2004 | Cohen-Bacrie et al. | |
| 2005/0228279 A1 | 10/2005 | Ustuner et al. | |
| 2006/0054824 A1 | 3/2006 | Federici et al. | |
| 2006/0238067 A1* | 10/2006 | Dausch | B06B 1/0622 310/311 |
| 2007/0016026 A1* | 1/2007 | Thomenius | G01S 7/5208 600/437 |
| 2007/0287918 A1* | 12/2007 | Huang | B06B 1/0238 367/181 |
| 2008/0013405 A1* | 1/2008 | Moon | B06B 1/0629 367/92 |
| 2010/0327695 A1* | 12/2010 | Goel | B06B 1/0622 310/320 |
| 2013/0109971 A1 | 5/2013 | Dahl et al. | |
| 2013/0293065 A1* | 11/2013 | Hajati | B06B 1/0629 310/334 |
| 2013/0294202 A1* | 11/2013 | Hajati | H01L 41/0825 367/138 |
| 2015/0097468 A1* | 4/2015 | Hajati | H01L 41/0825 310/334 |

OTHER PUBLICATIONS

Prince et al., "Medical Imaging Signals and Systems". Pearson ©2005. Cover and pp. vii-xiv and 347-378.*
Bamber, Jeffrey C. et al., "B-mode Speckle Texture: The Effect of Spatial Coherence," Acoustical Imaging, vol. 24, 2000, Kluwer Academic/Plenum Press, pp. 141-146.
Bamber, Jeffrey C. et al., "Spatial Coherence and Beamformer Gain," Acoustical Imaging, vol. 24, Kluwer Academic/Plenum Press, 2000, pp. 43-48.
Brunke, Shelby S. et al., "An Ultrasound Research Interface for a Clinical System," IEEE Transactions on Ultrasonics, Ferroelectrics, and Frequency Control, vol. 54, Issue 1, IEEE, Jan. 2007, pp. 198-210.
Camacho, Jorge et al., "Phase Coherence Imaging," IEEE Transactions on Ultrasonics, Ferroelectrics and Frequency Control, vol. 56, Issue 5, IEEE, May 2009, pp. 958-974.
Dahl, Jeremy J. et al., "Adaptive Imaging and Spatial Compounding in the Presence of Aberration," IEEE Transactions on Ultrasonics, Ferroelectrics and Frequency Control, vol. 52, Issue 7, Jul. 2005, IEEE, pp. 1131-1144.
Dahl, Jeremy J. et al., "Spatial and Temporal Aberrator Stability for Real-Time Adaptive Imaging," IEEE Transactions on Ultrasonics, Ferroelectrics and Frequency Control, vol. 52, Issue 9, Sep. 2005, IEEE, pp. 1504-1517.
Flax, S. W. et al., "Phase-Aberration Correction Using Signals From Point Reflectors and Diffuse Scatterers: Basic Principles," IEEE Transactions on Ultrasonics, Ferroelectrics and Frequency Control, vol. 35, Issue 6, Nov. 1988, IEEE, pp. 758-767.
Geiman, B. J. et al., "In Vivo Comparison of Fundamental and Harmonic Lateral Transmit Beam Shapes," 2000 IEEE Ultrasonics Symposium, vol. 2, Oct. 2000, IEEE, pp. 1669-1675.
Goodman, Joseph W., "Statistical Optics," (book) Wiley-Interscience, John Wiley & Sons, Inc., 2000, 567 pages.
Hollman, K.W., et al., "Coherence Factor of Speckle from a Multi-Row Probe," Proceedings of the 1999 IEEE Ultrasoncis Symposium, vol. 2, Oct. 1999, IEEE, pp. 1257-1260.

Jensen, Jørgen Arendt et al., "Calculation of Pressure Fields from Arbitrarily Shaped, Apodized, and Excited UltrasoundTransducers," IEEE Transactions on Ultrasonics, Ferroelectrics, and Frequency Control, vol. 39, Issue 2, Mar. 1992, IEEE, pp. 262-267.
Jensen, Jørgen Arendt, "Field: A program for Simulating Ultrasound Systems," 10th Nordic-Baltic Conference on Biomedical Imaging, Biological Engineering and Computing, vol. 34, Supplement 1, Part 1, 1996, pp. 351-353.
Krishnan, Sriram et al., "Adaptive Compensation of Phase and Magnitude Aberrations," IEEE Transactions on Ultrasonics, Ferroelectrics and Frequency Control, vol. 43, Issue 1, Jan. 1996, IEEE, pp. 44-55.
Li, Pai-Chi et al., "Adaptive Imaging Using the Generalized Coherence Factor," IEEE Transactions on Ultrasonics, Ferroelectrics, and Frequency Control, vol. 50, Issue 2, Feb. 2003, IEEE, pp. 128-141.
Liu, Dong-Lai et al., "About the Application of the Van Cittert-Zernike Theorem in Ultrasonic Imaging," IEEE Transactions on Ultrasonics, Ferroelectrics and Frequency Control, vol. 42, Issue 4, Jul. 1995, IEEE, pp. 590-601.
Mallart, Raoul et al., "Adaptive focusing in scattering media through sound-speed inhomogeneities: The van CittertZernike approach and focusing criterion," The Journal of the Acoustical Society of America, vol. 96, Issue 6, Dec. 1994, Acoustical Society of America, pp. 3721-3732.
Mallart, Raoul et al., "The van Cittert-Zernike theorem in pulse echo measurements," The Journal of the Acoustical Society of America, vol. 90, Issue 5, Nov. 1991, Acoustical Society of America, pp. 2718-2727.
Måsøy, Svein-Erik, "Estimation and correction of aberration in medical ultrasound imaging," Doctoral thesis, Norwegian University of Science and Technology, Oct. 2004, 136 pages, http://folk.ntnu.no/sveinmas/filer/avhandling_web.pdf.
O'Donnell, M. et al., "Phase-Aberration Correction Using Signals From Point Reflectors and Diffuse Scatterers: Measurements," IEEE Transactions on Ultrasonics, Ferroelectrics and Frequency Control, vol. 35, Issue 6, Nov. 1988, IEEE, pp. 768-774.
Walker, William F. et al., "The Application of K-space in Pulse Echo Ultrasound," IEEE Transactions on Ultrasonics, Ferroelectrics and Frequency Control, vol. 45, Issue 3, May 1998, IEEE, pp. 541-558.
Walker, William F. et al., "Speckle coherence and implications for adaptive imaging," Journal of the Acoustical Society of America, vol. 101, Issue 4, Apr. 1997, Acoustical Society of America, pp. 1847-1858.
International Search Report and Written Opinion for International Patent Application No. PCT/US2011/030516, dated Jun. 2, 2011, 9 pages.
International Preliminary Report on Patentability for International Patent Application No. PCT/US2011/030516, dated Oct. 11, 2012, 8 pages.
Non-Final Office Action for U.S. Appl. No. 13/638,996, dated Jul. 2, 2014, 11 pages.
Final Office Action for U.S. Appl. No. 13/638,996, dated Nov. 18, 2014, 13 pages.
Notice of Allowance and Examiner-Initiated Interview Summary for U.S. Appl. No. 13/638,996 dated Apr. 15, 2015, 10 pages.
Chou, Derrick R., "Piezoelectric Micromachined Ultrasound Transducers for Medical Imaging," Department of Biomedical Engineering Duke University, 2011, 245 pages.

* cited by examiner

PMUT ARRAY FOR ULTRASONIC IMAGING, AND RELATED APPARATUSES, SYSTEMS, AND METHODS

PRIORITY INFORMATION

This application claims the benefit of U.S. Provisional Patent Application Ser. No. 61/954,750, entitled "Improved Ultrasound Imaging Arrays and Methods of Use," filed Mar. 18, 2014, the disclosure of which is hereby incorporated herein by reference in its entirety for all purposes.

BACKGROUND

Field of the Disclosure

The disclosure relates to Piezoelectric Micromachined Ultrasound Transducer (pMUT) arrays for ultrasonic imaging, and related apparatuses, systems, and methods.

Technical Background

Ultrasound has continued to be one of the major medical diagnostic technologies. Sophisticated systems have evolved over the years which permit real time dynamic imaging in two-dimensions (2D) and in three dimensions (3D). In pulse-echo imaging, the returned echoes and echo images can be processed to quantify tissue and blood motion and other quantities. All of these systems utilize an ultrasound transducer or transducers which bi-directionally convert mechanical energy into electrical signals.

In a conventional method referred to as pulse-echo imaging, an ultrasound beam is propagated and formed from an array of elements by each array element emitting a pulse. Each emitted pulse is delayed by a predetermined amount, to steer or focus the beam, or both. Some of the acoustic energy is reflected back to the array elements due to a change in impedance caused by the differing materials in the targets. By summing appropriately delayed pulses received, a 2D slice or a 3D volume of the target may be imaged.

Conventional ultrasound transducer arrays use machined lead zirconium titanate (PZT) thickness mode vibrator elements formed by dicing a block of PZT with a microcircuit saw to form individual transducer elements. However, current dicing techniques are unable to produce PZT thickness mode vibrator elements suitable for transmitting and receiving at frequencies above 5-6 MegaHertz (MHz). As the desired frequency increases, the thickness of a conventional thickness mode vibrator element must be reduced. Below a certain thickness and surface area, the conventional dicing process destroys the thickness mode vibrator elements as they are being cut. Thus, it becomes impractical to produce thickness mode vibrator elements smaller than 175-200 microns $(\mu m)^2$ that are capable of transmitting and receiving mode vibrations above 5-6 MHz. Thus, there is a need in the art for improved ultrasound imaging arrays having smaller sizes and having ultrasound transmission and reception capability at higher frequencies.

SUMMARY OF THE DETAILED DESCRIPTION

Embodiments of the disclosure relate to Piezoelectric Micromachined Ultrasound Transducer (pMUT) arrays for ultrasonic imaging. Related apparatuses, systems, and methods are also disclosed. In one embodiment, an ultrasonic imaging assembly comprises a substrate and a plurality of array elements arranged on the substrate in an array. Each array element comprises at least one pMUT disposed on the substrate. The geometry of each pMUT, which may include a surface area, membrane thickness, shape and resonant cavity volume, and/or other factors, dictates a fundamental mode vibration for the pMUT. Each pMUT has a predetermined geometry configured to accept a specific fundamental mode vibration corresponding to a desired transmit and receive mode vibration for the pMUT. While it is possible to vibrate a pMUT at a number of different mode vibrations, i.e., harmonic mode vibrations, the performance of the pMUT is most predictable and efficient when vibrated at the fundamental mode vibration of the pMUT. Thus, by configuring the geometry of the pMUT such that the fundamental mode vibration of the pMUT corresponds to a desired transmit and receive mode vibration, the performance of the pMUT array is improved.

The plurality of array elements are configured to transmit and receive at least one ultrasound beam based on the predetermined fundamental mode vibration. By configuring the geometry of the pMUTs to correspond to a desired fundamental mode vibration, the pMUT array has improved sensitivity, and can be produced relatively inexpensively compared to dicing methods used for conventional thickness mode vibration transducers. One non-limiting advantage of this arrangement is that the smaller element size of the pMUT allows for a pMUT array that has a significantly smaller surface area and thickness than conventional thickness mode vibration transducer arrays (e.g., by a factor of two (2) or more). In addition, the smaller area and thickness of the individual pMUT transducers relative to conventional thickness mode vibration transducers allow for a corresponding increase in the fundamental mode vibration for each pMUT. This allows for pMUT sizes of less than 100 (micrometers) $\mu m$ in length for typical ultrasound diagnostic frequencies in the 2 MegaHertz (MHz) to 10 MHz range, and as small as 30 $\mu m$ in length for higher frequencies of 10 MHz to 30 MHz. Compared to the effective 175-200 $\mu m$ length and 5-6 MHz limits of conventional thickness mode vibration transducers, this represents a significant improvement in both size and mode vibration response over conventional ultrasound arrays.

In this regard, in one embodiment, an ultrasonic imaging assembly is provided. The ultrasonic imaging assembly comprises a substrate and a plurality of pMUT array elements arranged on the substrate in an array. Each pMUT array element has a predetermined geometry configured to accept a predetermined fundamental mode vibration. Each array element comprises at least one piezoelectric layer disposed on the substrate. Each array element further comprises at least one first electrode connected between the at least one piezoelectric layer and a signal conductor. Each array element further comprises at least one second electrode connected between the at least one piezoelectric layer and a ground. The plurality of array elements are configured to transmit and receive at least one ultrasound beam having a bandwidth including the predetermined fundamental mode vibration of each of the plurality of pMUT array elements.

In another embodiment, an ultrasonic imaging apparatus is disclosed. The ultrasonic imaging apparatus comprises an ultrasonic imaging sub-assembly comprising a substrate and a plurality of pMUT array elements arranged on the substrate in an array. Each pMUT array element has a predetermined geometry configured to accept a predetermined fundamental mode vibration. Each array element comprises at least one piezoelectric layer disposed on the substrate. Each array element further comprises at least one first electrode connected between the at least one piezoelectric layer and a signal conductor. Each array element further comprises at least one second electrode connected between the at least one piezoelectric layer and a ground conductor. The ultrasonic imaging apparatus further comprises a controller in communication with the signal trace of the ultrasonic imaging sub-assembly. The controller is configured to direct the array elements, via the signal trace, to transmit and receive, with respect to an object, at least one ultrasound beam having a bandwidth including the predetermined fundamental mode vibration of each of the plurality of pMUT array elements. The controller is further configured to receive at least one signal from the array elements based on transmitting and receiving the at least one ultrasound beam. The controller is further configured to construct at least one image of at least a portion of the object based on the at least one signal.

In another embodiment, a method of imaging a portion of an object is disclosed. The method comprises transmitting and receiving, with respect to an object, at least one ultrasound beam having a bandwidth including a fundamental mode vibration of each of at least one pMUT of a plurality of array elements. Each pMUT array element comprises at least one piezoelectric layer disposed on the substrate. Each pMUT array element has a predetermined geometry configured to accept a predetermined fundamental mode vibration. The method further comprises receiving, at a controller, at least one signal from the plurality of array elements based on transmitting and receiving the at least one ultrasound beam. The method further comprises constructing at least one image of at least a portion of the object based on the at least one signal.

Additional features and advantages will be set forth in the detailed description which follows, and in part will be readily apparent to those skilled in the art from that description or recognized by practicing the embodiments as described herein, including the detailed description that follows, the claims, as well as the appended drawings.

It is to be understood that both the foregoing general description and the following detailed description present embodiments, and are intended to provide an overview or framework for understanding the nature and character of the disclosure. The accompanying drawings are included to provide a further understanding, and are incorporated into and constitute a part of this specification. The drawings illustrate various embodiments, and together with the description serve to explain the principles and operation of the concepts disclosed.

DETAILED DESCRIPTION

Reference will now be made in detail to the embodiments, examples of which are illustrated in the accompanying drawings, in which some, but not all embodiments are shown. Indeed, the concepts may be embodied in many different forms and should not be construed as limiting herein; rather, these embodiments are provided so that this disclosure will satisfy applicable legal requirements. Whenever possible, like reference numbers will be used to refer to like components or parts.

Embodiments of the disclosure relate to Piezoelectric Micromachined Ultrasound Transducer (pMUT) arrays for ultrasonic imaging. Related apparatuses, systems, and methods are also disclosed. In one embodiment, an ultrasonic imaging assembly comprises a substrate and a plurality of array elements arranged on the substrate in an array. Each array element comprises at least one pMUT disposed on the substrate. The geometry of each pMUT, which may include a surface area, membrane thickness, shape and resonant cavity volume, and/or other factors, dictates a fundamental mode vibration for the pMUT. Each pMUT has a predetermined geometry configured to accept a specific fundamental mode vibration corresponding to a desired transmit and receive mode vibration for the pMUT. While it is possible to vibrate a pMUT at a number of different mode vibrations, i.e., harmonic mode vibrations, the performance of the pMUT is most predictable and efficient when vibrated at the fundamental mode vibration of the pMUT. Thus, by configuring the geometry of the pMUT such that the fundamental mode vibration of the pMUT corresponds to a desired transmit and receive mode vibration, the performance of the pMUT array is improved.

Exemplary equations for calculating a fundamental mode vibration of a pMUT based on the physical dimensions of a pMUT may be found, for example, in "Piezoelectric Micromachined Ultrasound Transducers for Medical Imaging" by Derrick R. Chou, pages 195-196, which is hereby incorporated by reference for this purpose. It is similarly possible, using these and other techniques, to design a pMUT imaging transducer having a predetermined geometry corresponding to a target fundamental mode vibration.

The plurality of array elements are configured to transmit and receive at least one ultrasound beam based on the predetermined fundamental mode vibration. By sizing the pMUTs to correspond to a desired fundamental mode vibration, the pMUT array has improved sensitivity, and can be produced relatively inexpensively compared to other dicing methods. One non-limiting advantage of this arrangement is that the smaller element size of the pMUT allows for pMUT arrays that are significantly smaller surface area than conventional thickness mode vibrator transducer arrays (e.g., by a factor of two (2) or more). In addition, the smaller geometry of the pMUT transducers allow for a corresponding increase in fundamental mode vibration for each array element. This allows for pMUT sizes of less than 100 (micrometers) µm in length for typical ultrasound diagnostic frequencies in the 2 MegaHertz (MHz) to 10 MHz range, and as small as 30 µm in length for higher frequencies of 10 MHz to 30 MHz. Compared to the effective 175-200 µm length and 5-6 MHz limits of conventional thickness mode vibrator transducers, this represents a significant improvement in both size and mode vibration response over conventional ultrasound arrays.

Figure 1:
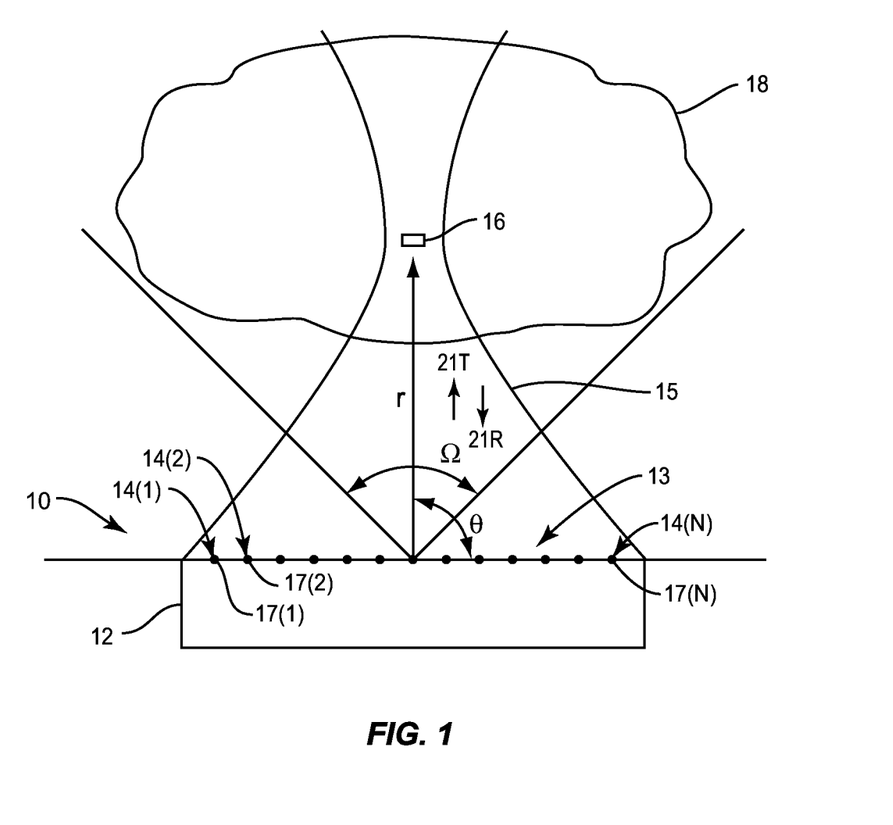
FIG. 1 is a schematic diagram of an exemplary ultrasonic imaging assembly employing a pMUT imaging array to transmit and receive an ultrasonic beam according to an exemplary embodiment.

In this regard, FIG. 1 is a schematic diagram of an exemplary ultrasonic imaging assembly employing a pMUT array to transmit and receive an ultrasonic beam according to an exemplary embodiment. The ultrasonic imaging assembly 10 comprises a substrate 12 and an array 13 of N array elements 14(1)-14(N) arranged on the substrate 12. The Piezoelectric Micromachined Ultrasound Transducer (pMUT) array elements 14(1)-14(N) are configured to transmit and receive an ultrasound beam 15 with respect to a volume element 16 in a target 18. As will be described in more detail below with respect to FIGS. 2A and 2B, each pMUT array element 14 comprises at least one pMUT 17 disposed on the substrate 12. Each pMUT 17(1)-17(N) has a predetermined geometry configured to accept a predetermined fundamental mode vibration corresponding to a desired bandwidth of the at least one ultrasound beam.

As discussed above, the overall geometry of each pMUT 17 dictates a fundamental mode vibration for the pMUT 17, which is the lowest frequency at which the pMUT 17 is able to produce or receive a coherent vibration. Vibrating a pMUT 17 at a higher mode vibrations, corresponding to harmonic frequencies of the fundamental frequency, is also possible. Here, however, each pMUT can be sized at a small enough geometry that the fundamental mode vibration can be used as the transmit and receive mode vibration, thereby enhancing the performance and predictability of the pMUT array.

In the embodiment of FIG. 1, the ultrasound beam 15 is propagated by emitting a pulse, such as a pulse signal, for example, from each of array elements 14(1)-14(N) with each emitted pulse delayed by a predetermined amount. Depending on the delay utilized, an acoustic beam 15 of transmitted energy 21T can be aimed in a direction ⊖ and focused onto the target 18. When the acoustic energy 21T is reflected, due to a change in impedance caused by the presence of volume element 16 in the target 18, for example, some of the transmitted acoustic energy 21T is reflected back to the array elements 14 as reflected acoustic energy 21R. By summing appropriately delayed pulses received by the array elements 14, an amplitude of the echo from the volume element 16 or other elements in target 18 can be calculated. This technique is commonly referred to as pulse-echo imaging.

By controlling the delays for a plurality of pulses, a 2D slice of the target 18 may be imaged by scanning angularly back and forth across a plane, referred to as an azimuth plane, extending outward from the ultrasonic imaging assembly 10. Such scanning, referred to as B-mode scanning, returns a reflectance value for a range of distances r across an angle Ω When the reflectance value for all points in the plane corresponding to a distance r at an angle Ω are translated into planar coordinates, an image is formed of pixels having an X and Y coordinate with the value of each pixel related to an amplitude of the echo received from a corresponding differential volume element 16 of the target 18. When the target 18 is biological tissue, for example, different features having different densities or compressibilities can be detected as distinct volume elements 16. In this manner, ultrasound images of biological tissue can be interpreted to determine the relative and absolute location and the acoustic reflectivity of different tissue types such as bone, soft tissue, tendons, and the like.

As discussed above, conventional transducer arrays use machined PZT thickness mode vibrator elements formed by dicing a block of PZT with a microcircuit saw to form individual transducer elements. However, current dicing techniques are unable to produce PZT thickness mode vibrator elements suitable for transmitting and receiving at frequencies above 5-6 MHz. As the desired frequency increases, the thickness of a conventional thickness mode vibrator element must be reduced. Below a certain thickness and surface area, the thickness mode vibrator elements can be destroyed as they are cut using the conventional dicing process. Thus, it becomes impractical to produce thickness mode vibrator elements smaller than 175-200 µm$^2$ that are capable of transmitting and receiving mode vibrations above 5-6 MHz.

In contrast, pMUT arrays are membrane-based vibrators that are disposed directly on a substrate using Microelectromechanical Systems (MEMS) or similar manufacturing techniques. Thus, a potentially destructive mechanical dicing process is not necessary. The individual array elements can be made significantly smaller than what is possible for conventional thickness mode vibrator elements. This has a number of advantages over conventional thickness mode vibrator element arrays. First, the smaller element size allows for pMUT transducer arrays that are significantly smaller than conventional transducer arrays. Second, and just as importantly, the smaller geometry of the pMUT transducers allow for a corresponding increase in mode vibration frequency. This results in pMUT sizes of less than 100 µm in length for typical ultrasound diagnostic frequencies in the 2 MHz to 10 MHz range, and as small as 30 µm in length for higher frequencies of 10 MHz to 30 MHz. Compared to the effective 175-200 µm and 5-6 MHz limits of conventional thickness mode vibrator transducers, this represents a significant improvement in both size and mode vibration response.

Details of an exemplary construction of a pMUT element array that can be used to produce the pMUT array elements 14(1)-14(N) in FIG. 1 are taught in U.S. Pat. No. 7,449,821 to Dausch, the contents of which are hereby incorporated by reference for this purpose. As noted above with respect to FIG. 1, pMUTs are membrane vibrators and are also active components. As will be described in detail below with respect to FIGS. 2A and 2B, by disposing and sandwiching a piezoelectric film between a signal electrode and ground electrode over a thinned section of the substrate, the pMUT can be caused to launch an acoustic wave by sending a signal from a controller to the signal electrode at a predetermined mode vibration. The acoustic wave may be reflected back toward the pMUT, for example by a volume element 16 in target 18, and absorbed by the pMUT, where the acoustic energy is converted back into electrical energy and transmitted to the controller. It is desirable to transmit and receive acoustic energy using the fundamental mode vibration of the pMUT, which is in turn determined by the geometry of the pMUT, including surface area, membrane thickness, and resonance cavity size. While it is possible to transmit acoustic energy at higher frequencies using harmonic mode vibrations of a given pMUT, these harmonic modes are less predictable than the fundamental mode vibration for a given pMUT geometry. Harmonic mode vibrations also produce less acoustic energy than the fundamental mode vibration for a given pMUT geometry. Thus, transmitting and receiving acoustic energy at the fundamental mode vibration of the pMUTs will achieve optimal pMUT performance.

pMUTs have a number of other advantages over conventional thickness mode vibrator elements as well. For example, one effect of the smaller size and thickness of a pMUT is that the electrical impedance of the piezoelectric film is significantly lower than the electrical impedance of a conventional thickness mode vibrator element. In addition, thickness of the piezoelectric film is only weakly correlated with the fundamental mode vibration of the pMUT compared to other geometric factors such as membrane thickness and surface area. As a result, unlike conventional thickness mode vibrator elements, electrical impedance of the piezoelectric film can be tuned via changes in film thickness without significantly affecting the fundamental mode vibration of the pMUT element. This allows greater customization and optimization of the element.

Figure 2A:
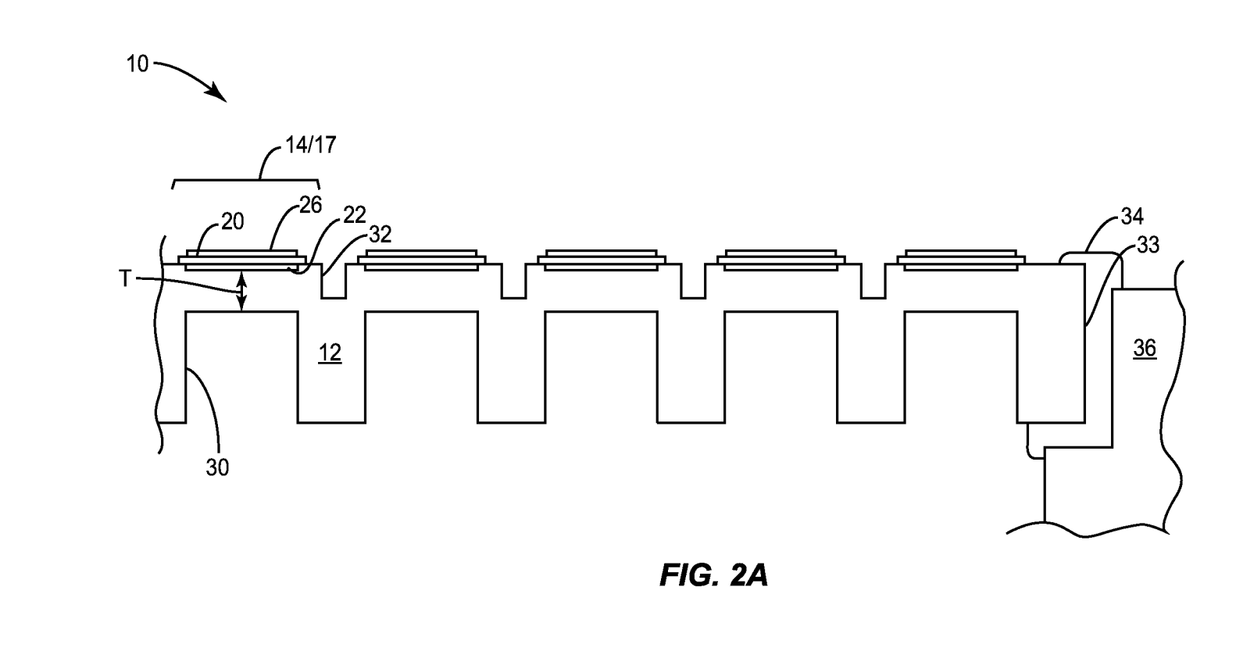
FIG. 2A illustrates a cross-sectional schematic view of the imaging assembly of FIG. 1, according to an exemplary embodiment.
Figure 2B:
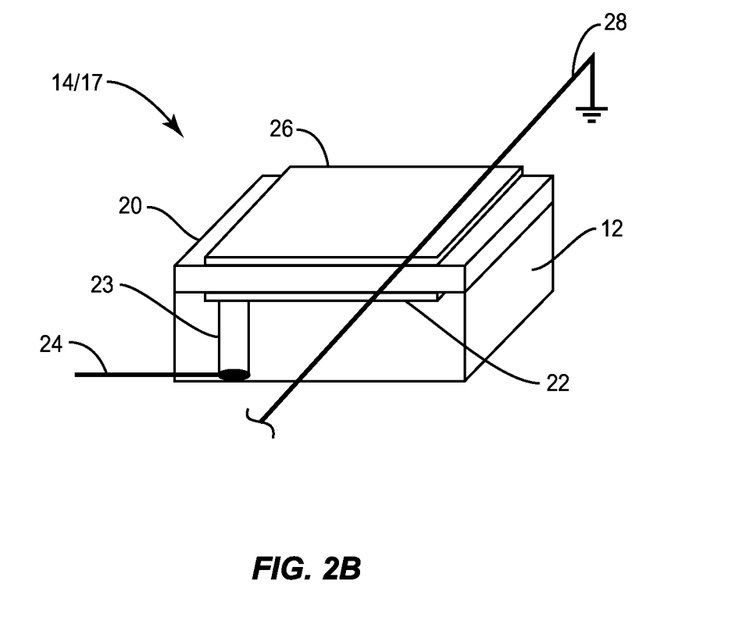
FIG. 2B illustrates a detailed perspective schematic view of an exemplary array element of the imaging assembly of FIG. 2A, according to an exemplary embodiment.

In this regard, FIG. 2A illustrates a cross-sectional schematic view of imaging assembly 10 according to the embodiment of FIG. 1. FIG. 2B illustrates a detailed perspective schematic view of a single pMUT array element 14 according to the embodiment of FIG. 1. As shown by FIG. 2A, each array element 14 includes a first conductor 22, e.g., a signal electrode, disposed on the substrate 12. As shown in FIG. 2B, the first conductor 22 is connected to a conductive via 23 in the substrate 12, which is in turn connected to a signal trace 24 for transmitting and receiving electrical signals. The piezoelectric film 20 is disposed over the first conductor 22. The film 20 may be formed from any suitable material, including lead zirconium titanate (PZT).

With continuing reference to FIG. 2B, a second conductor 26, e.g., a ground electrode, is disposed over the piezoelectric film 20. The second conductor 26 is connected to a ground trace 28, which is connected to a common ground. By transmitting a transmit signal Tx over signal trace 24, the piezoelectric film 20 causes the pMUT 17 to resonate at a mode vibration based on the transmit signal and emits acoustic energy based on the mode vibration. Acoustic energy that is reflected back toward the pMUT 17 by a volume element is then absorbed by the pMUT 17 and converted back into electrical energy and provided to the signal trace 24 as a receive signal Rx. As discussed above, by employing the fundamental mode vibration of the pMUT 17, acoustic energy is transmitted at a higher efficiency, and can also be more efficiently received when the acoustic energy is reflected back toward the pMUT 17.

With reference back to FIG. 2A, to increase pMUT 17 performance, a well 30 may be etched into the substrate 12 on a side opposite from the piezoelectric film 20 and aligned with the film 20 such that a portion of the substrate 12 under each film 20 has a thickness T less than the thickness of the overall substrate 12. Providing the well 30 reduces the thickness of silicon substrate 12 under the piezoelectric film 20, thereby allowing the pMUT 17 to resonate more freely. The well 30 provides a resonant cavity, which may also increase pMUT 17 performance by allowing the pMUT 17 to emit and receive acoustic energy more efficiently.

However, using pMUTs in an ultrasonic imaging array introduces its own set of challenges. In particular, the small size of the pMUT elements makes it much more difficult to eliminate and filter out noise and interference, such as from harmonic frequencies, cross-coupling, substrate rumble, or environmental conditions, because such interference is much larger in comparison to the transmitted and received acoustic energy 21T/R from each individual pMUT 17. In particular, restricting pMUT sizes to permit transmission and reception of only fundamental mode vibrations causes significant increases in performance and predictability from pMUT array elements when used in an ultrasound imaging array.

One problem that arises when transmitting and receiving acoustic energy with elements at this scale is that it is much easier for small amounts of interference and background noise to overwhelm the transmitted and received acoustic energy. For example, the close physical proximity of pMUTs 17 in the array can lead to cross-coupling interference between the individual pMUTs 17, which corrupts and degrades the quality of pMUT 17 output in both the transmit and receive directions. Cross-coupling may be caused by acoustic energy propagating from one pMUT 17 through the substrate 12 and into adjacent pMUTs. To alleviate this problem, Applicant has recognized that physical decoupling of the individual pMUTs 17 reduces acoustic interference between these individual pMUTs 17. In one embodiment, trenches 32 may be etched into the substrate 12 between adjacent pMUTs 17, which cause acoustic energy propagating from the pMUT 17 through the substrate 12 to be reflected back and/or dissipated at the trench 32 boundary, rather than continuing through the substrate and interfering with acoustic performance of adjacent pMUTs 17. In one embodiment, the impedance mismatch caused by the trench 32 boundary may be sufficient to reduce cross-coupling. In another embodiment, the trench 32 may be filled with damping materials, such as air-filled micro-spheres, to further absorb and dissipate unwanted acoustic energy.

Figure 3:
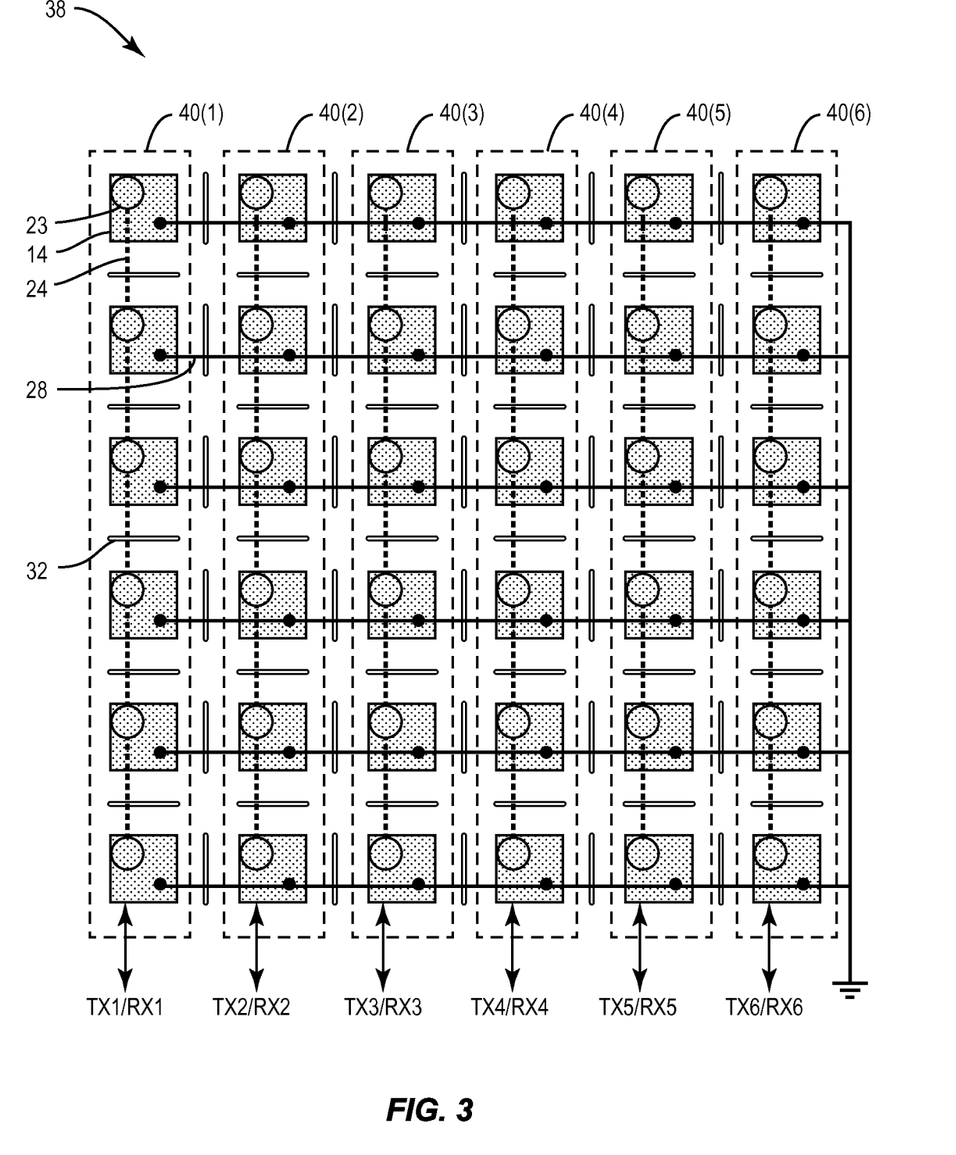
FIG. 3 illustrates a schematic diagram of an exemplary 1D ultrasonic pMUT imaging array according to an exemplary embodiment.

Another problem that may arise when using pMUTs 17 at this scale is that the substrate 12 may contain a low frequency rumble caused by acoustic energy propagating through the substrate and reflecting off the substrate boundary 33 at the edge of the array due to the mechanical impedance change at the substrate boundary 33. Applicant has recognized that providing a damping material 34, such as polyimide, between the substrate boundary 33 and a transducer support 36 or other mounting surface can significantly reduce this low frequency rumble by absorbing the low frequency acoustic energy at the substrate boundary 33. Another advantage of this damping material 34 is that it can prevent background environmental noise and vibration from entering the substrate from the transducer support 36 or other hardware.

pMUT imaging arrays can be used for a wide variety of ultrasound imaging applications. In this regard, FIG. 3 illustrates a schematic diagram of an exemplary 1D ultrasonic pMUT imaging array 38 ("1D array 38"). In this embodiment, the 1D array 38 has thirty-six (36) array elements 14 arranged in a 6×6 array, but it should be understood that larger or smaller arrays are possible. It may be desirable to have a large array size, as large as 20 mm or larger in some applications. Thus, it may be desirable to interconnect multiple array elements 14 to act as a single, larger 1D array element 40. By combining multiple array elements 14 into a single 1D array element 40, beam response and resolution in the nonscanned, i.e., elevation, dimension may be improved.

Here, the individual array elements 14 are grouped into six (6) 1D array elements 40(1)-40(6), with each 1D array element 40 comprising a column of six (6) array elements 14 connected to a common signal trace 24. The array elements 14 are also all connected to a common ground trace 28. The six (6) 1D array elements 40(1)-40(6) are arranged in a row to scan across an azimuth direction (which is the horizontal direction in FIG. 3). The 1D array 38 is configured to scan an ultrasound beam in an azimuth arc. A plane defined by the scanning of the ultrasound beam defines an azimuthally scanned plane that is substantially parallel to the azimuth direction and is substantially perpendicular to the plane defined by the 1D array 38.

While a 1D array allows for a minimal number of signal traces, it may also be desirable to allow for some degree of independent transmission with respect to the elevation direction as well. In one arrangement, referred to as a 1.5D array, elements in the elevation direction may be employed to focus the ultrasound beam, thereby reducing the thickness of the beam with respect to the azimuthally scanned plane and increasing the resolution of the resultant image.

Figure 4:
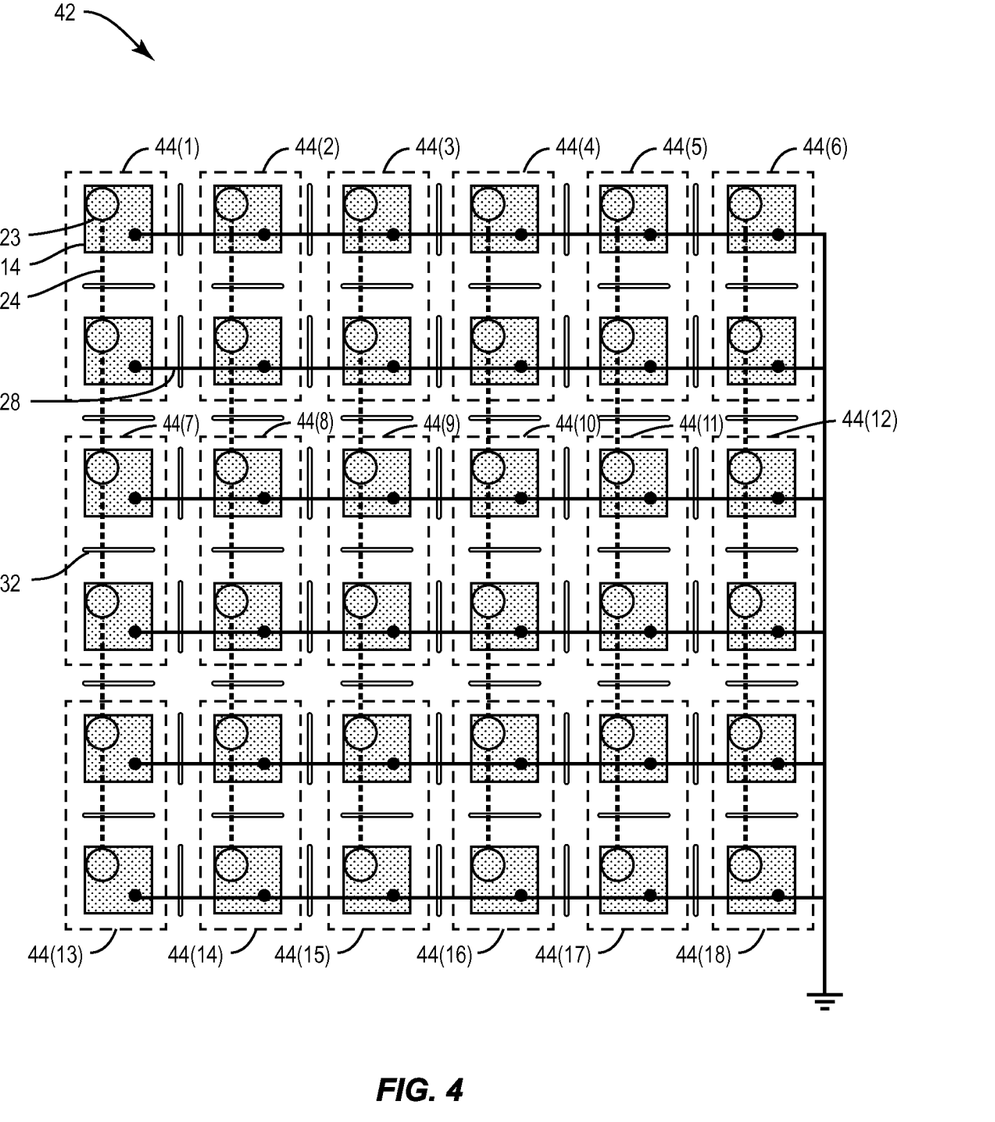
FIG. 4 illustrates a schematic diagram of an exemplary 1.5D ultrasonic pMUT imaging array according to an exemplary embodiment.

In this regard, FIG. 4 illustrates a schematic diagram of an exemplary 1.5D ultrasonic pMUT imaging array 42 ("1.5D array 42"). As with 1D array 38 of FIG. 3, the 1.5D array 42 of FIG. 4 has a plurality of array elements 14 arranged in a 6×6 array. Here, however, the array elements 14 are paired together to form eighteen (18) 1.5D array elements 44(1)-44(18) arranged in three (3) rows of six (6) 1.5D array elements 44. In this embodiment, each row extends in the azimuth direction (which is the horizontal direction in FIG. 4) and the rows are stacked in the elevation direction (which is the vertical direction in FIG. 4). The center row of 1.5D array elements 44(7)-44(12) is configured to scan in the azimuth direction similar to the 1D array elements 40(1)-40(6) of FIG. 3. Here, however, the upper row of 1.5D array elements 44(1)-44(6) and lower row of 1.5D array elements 44(13)-44(18) can be independently employed to focus the ultrasonic beam, thereby improving out-of-scan-plane resolution in the elevation dimension. This arrangement may also permit limited steering of the ultrasonic beam in the elevation dimension, while still minimizing the number of signal traces required to operate the 1.5D array 42.

Figure 5:
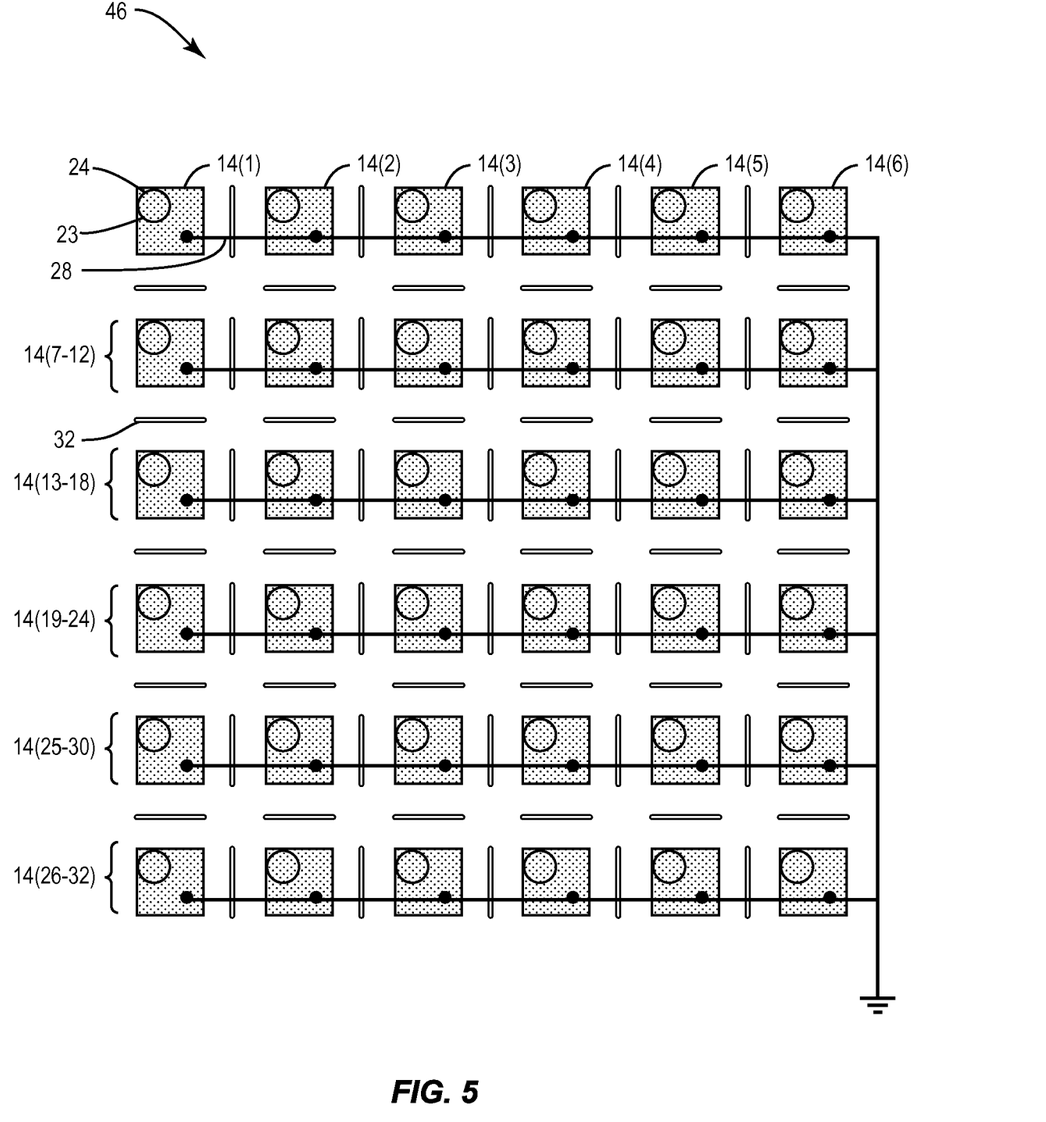
FIG. 5 illustrates a schematic diagram of an exemplary 2D ultrasonic pMUT imaging array according to an exemplary embodiment.

It may also be desirable to permit full steering of the ultrasonic beam in both the azimuth and the elevation directions. In this regard, FIG. 5 illustrates a schematic diagram of an exemplary 2D ultrasonic pMUT imaging array 46. In this embodiment, a plurality of array elements 14 is again arranged in a 6×6 array, but here, each array element 14 is connected to a unique signal trace, thereby allowing independent operation and timing control of each of the array elements 14. This arrangement allows the ultrasonic beam to be steered and directed along an elevation arc as well as an azimuth arc, which allows for creation of a true 3D image. This arrangement also allows for further manipulation of the ultrasonic beam, including moving the source of the ultrasonic beam vector in the azimuth and/or elevation direction, in order to image a target volume from a number of different angles, thereby improving image resolution and accuracy.

As discussed above, it may be desirable to combine a plurality of array elements 14 into a combined array element, such as a 1D array element as shown in FIG. 4 or a 1.5D array element as shown in FIG. 5. In these embodiments above, each array element 14 included one pMUT 17, and the individual array elements 14 were connected together in parallel. However, the number of array elements that is practical for an array may be limited by the number of wires between the array and a controller. Thus, in some embodiments, it may be desirable to group multiple pMUTs having different sizes together as a single array element, thereby increasing the total active area of the array, referred to as fill factor. In this regard, FIGS. 6A-6C illustrate array elements having multiple pMUTs according to a number of different exemplary embodiments.

Figure 6A:
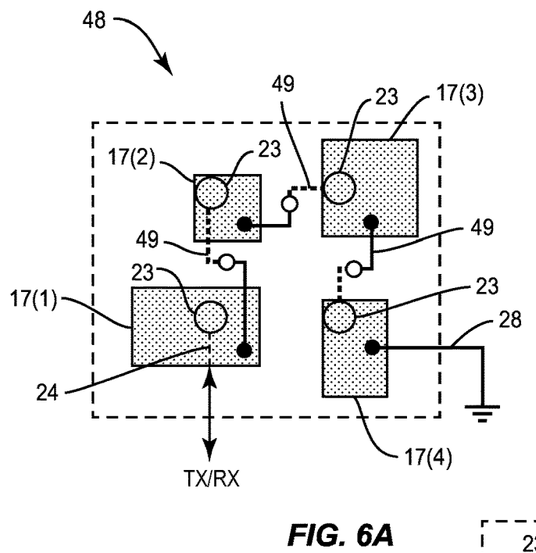
FIGS. 6A-6C illustrate array elements having multiple pMUTs of different sizes and different interconnection schemes, according to exemplary embodiments.
Figure 6B:
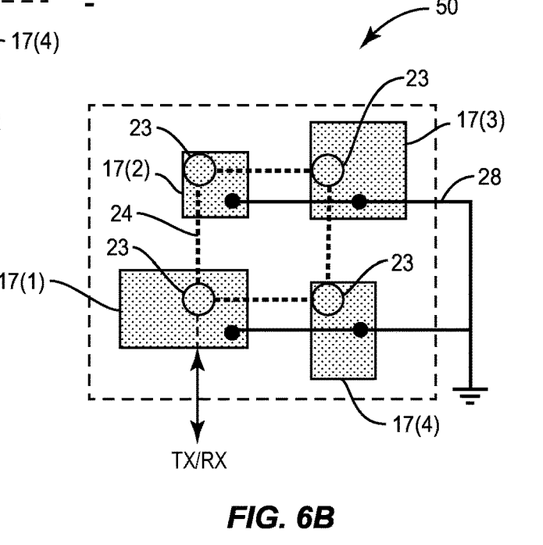
Figure 6C:
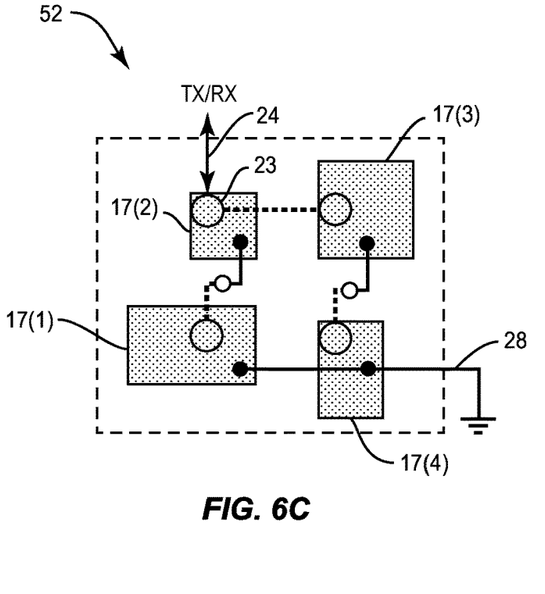

FIG. 6A illustrates an array element 48 having four pMUTs 17(1)-17(4), each having a different vibrational geometry. As a result, each pMUT has a different fundamental mode frequency. One advantage of this arrangement is that the acoustic energy emitted by the array element 48 will contain a number of different frequencies in the same pulse, thereby increasing the bandwidth of the pulse without increasing the pulse length. This is important because if the pulse length is too long, the acoustic energy will begin to be reflected back and received by the pMUTs 17 before the pMUTs 17 have finished emitting the pulse, causing interference and distorting the result. Thus, by transmitting multiple fundamental mode vibrations simultaneously, bandwidth and resolution can be increased while maintaining beam integrity. The shape of a pMUT also has an effect on resonant frequency and bandwidth. Circular, polygonal, elliptical and other shaped pMUTs can be used singly or interconnected to form a variety of different array elements, thereby increasing overall array bandwidth.

In the example of FIG. 6A, pMUTs 17(1)-17(4) are connected to each other in series. The physical dimensions and construction of the pMUTs 17 determine the amount of energy that can be transmitted or converted into the received signal. Since the pMUTs 17 must be relatively small to correspond to the required fundamental mode vibrations used in ultrasound applications, the active area of individual pMUTs 17 is relatively low. By connecting the individual pMUTs 17 in series and increasing the signal voltage accordingly, the acoustically active area of the array element 48 may be effectively increased.

Referring to FIG. 6A, the signal conductor of pMUT 17(1) is connected to signal trace 24 by via 23, and the ground conductor of pMUT 17(1) is connected to signal conductor of pMUT 17(2) by series trace 49. The ground conductor of pMUT 17(3) is similarly connected to signal conductor of pMUT 17(1), and the ground conductor of pMUT 17(2) is connected to signal conductor of pMUT 17(4), by series traces 49. The ground conductor of pMUT 17(4) is connected to ground trace 28. In this manner, the amplitude of acoustic energy that is transmitted and received by the array element 48 may be increased by increasing the source voltage, without the need for additional wires.

Referring now to FIG. 6B, it may also be desirable to instead connect individual pMUTs in parallel within a single array element. In this regard, array element 50 has four pMUTs 17(1)-17(4) connected in parallel. Here, the signal conductor of each pMUT 17 is connected to a common signal trace 24 by the vias 23, and the ground conductor of each pMUT 17 is connected to a common ground trace 28. This arrangement reduces the impedances of the individual pMUTs 17, thereby increasing the efficiency of the array element 50 while maintaining the same source voltage.

It may also be desirable to provide array elements that have pMUTs 17 connected in series and parallel at the same time. In this regard, FIG. 6C illustrates an array element 52 having four pMUTs 17(1)-17(4). Here, pMUTs 17(1) and 17(2) are connected in series, and pMUTs 17(3) and 17(4) are also connected in series by series traces 49 similar to FIG. 6A, and the two pairs of pMUTs 17 are connected in parallel between signal trace 24 and ground trace 28 similar to FIG. 6B. It should be understood that any number of different combinations of pMUT shapes, sizes and connection schemes may be employed in different array elements as desired.

Figure 7:
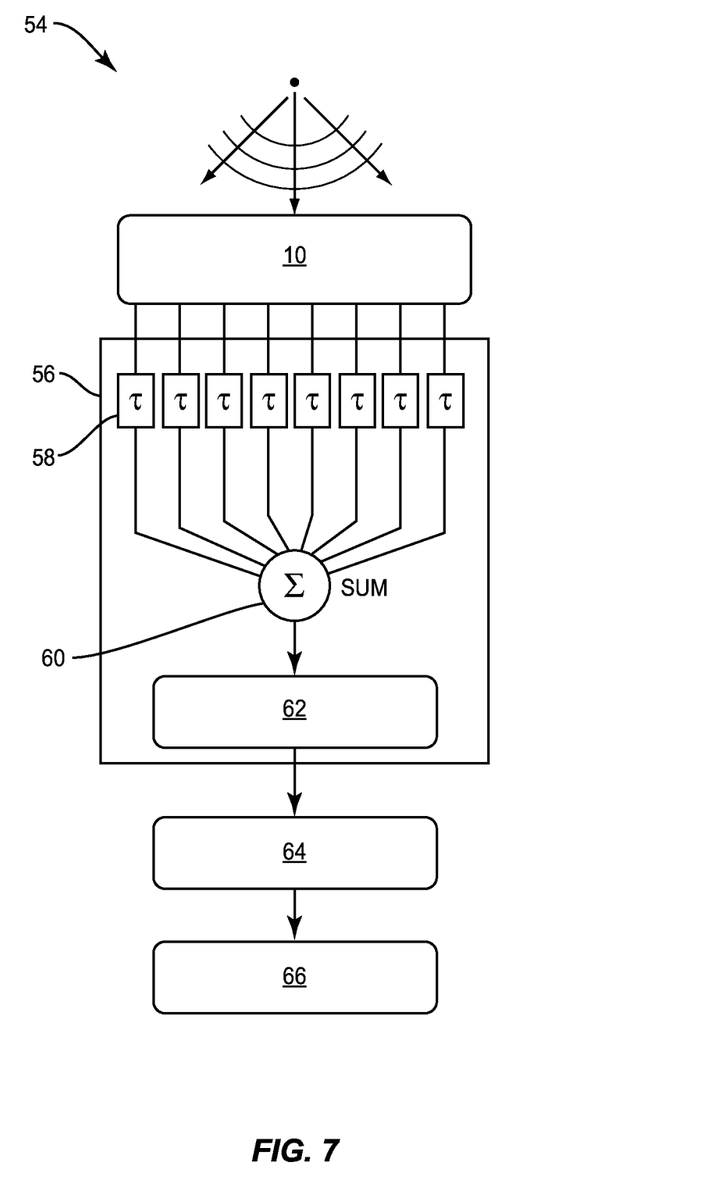
FIG. 7 illustrates a schematic diagram of an exemplary ultrasonic imaging apparatus having a pMUT ultrasound imaging array according to an exemplary embodiment.

As discussed above, the number of wires connected to an ultrasound imaging array may limit the size and applications of the imaging array. Thus, it may be desirable to configure the array as a multiplexed array, thereby reducing the total number of wires that must be connected to the array. In this regard, FIG. 7 illustrates a schematic diagram of an exemplary ultrasonic imaging apparatus 54 according to an exemplary embodiment. The apparatus 54 includes an ultrasonic imaging assembly 10 as described above, connected to a controller 56. The controller 56 is in communication with the signal traces of the ultrasonic imaging assembly 10 and is configured to direct the array elements, via the signal traces, to transmit and receive at least one ultrasound beam with respect to an object. The controller 56 is also configured to receive at least one signal from the array elements based on transmitting and receiving the at least one ultrasound beam. In this embodiment, the controller 56 applies a plurality of delays 58 to the signals received from the ultrasonic imaging assembly 10 and combines the signals using a sum function 60. The controller 56 next processes the combined signal using a B-mode image processor 62 to generate an image 64, which can be output to a display 66.

Figure 8:
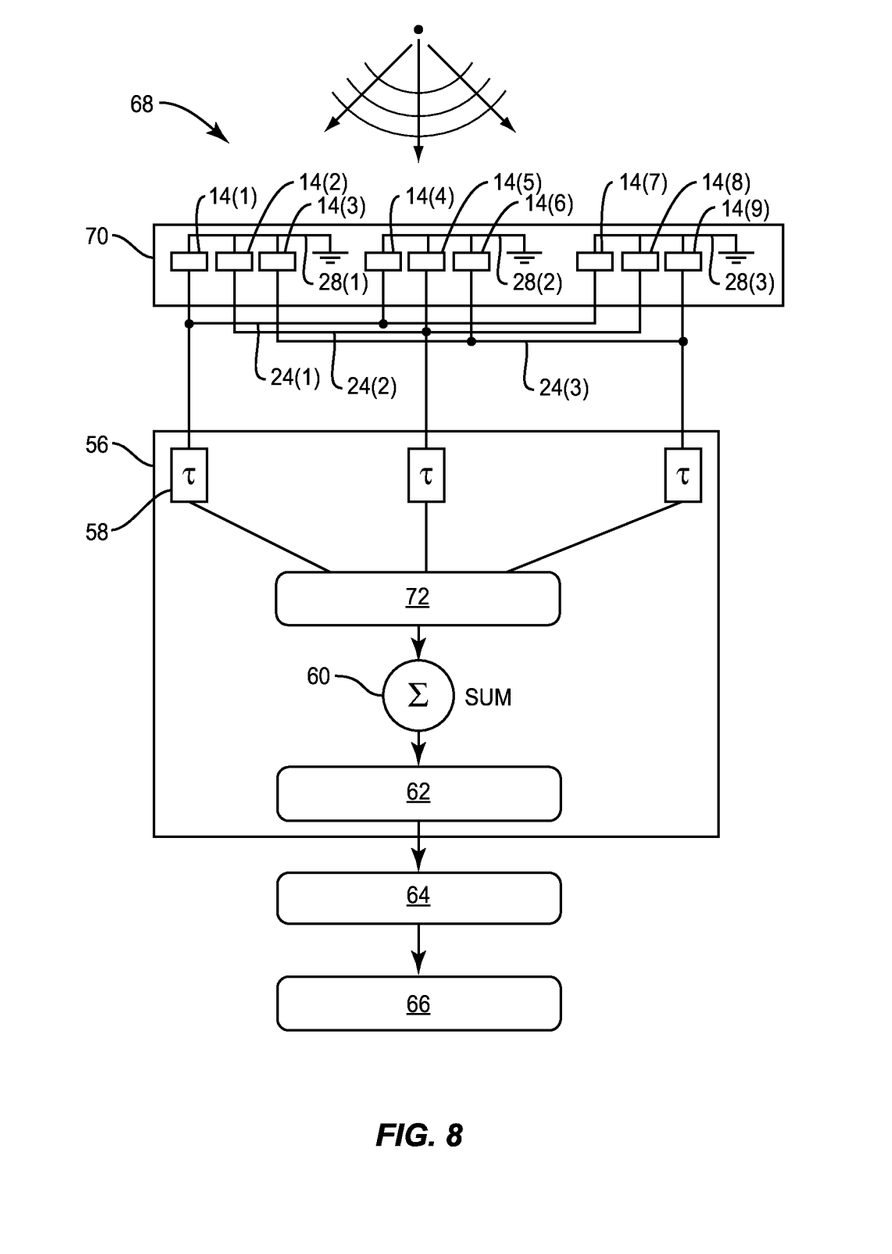
FIG. 8 illustrates a schematic diagram of an exemplary ultrasonic imaging apparatus having a multiplexed pMUT ultrasound imaging array according to an exemplary embodiment.

In one embodiment, the array elements of an ultrasonic imaging assembly may be multiplexed as distinct groups of array elements, each group of array elements being connected to a unique ground. In this regard, FIG. 8 illustrates a schematic diagram of an exemplary ultrasonic imaging apparatus 68 having a multiplexed pMUT ultrasound imaging array 70 according to an exemplary embodiment. In this embodiment, the array of nine (9) array elements 14(1)-14 (9) are multiplexed such that each array element 14 is connected to one of three common ground traces 28. For example, array elements 14(1)-14(3) are connected to ground trace 28(1), array elements 14(4)-14(6) are connected to ground trace 28(2), and array elements 14(7)-14(9) are connected to ground trace 28(3). Each array element 14 connected to a common ground is connected to a unique signal trace 24. For example, array elements 14(1), 14(4), and 14(7) are connected to signal trace 24(1), array elements 14(2), 14(5), and 14(8) are connected to signal trace 24(2), and array elements 14(3), 14(6), and 14(9) are connected to signal trace 24(3). By selectively activating and deactivating the different signal traces 24 and ground traces 28, the entire array 70 can be employed using a reduced number of of wires leading back to the controller 56.

In this embodiment, the controller further comprises a memory 72 for storing the time-delayed result from each of the array elements 14 as they are activated in sequence. Once results from all of array elements 14(1)-14(9) have been stored, the results can then be summed by the sum function 60 and output to the B-mode image processor 62 to generate an image 64. In this manner, the entire array can be employed without requiring a unique signal wire for each array element. This allows for a number of variations on the above described embodiments, including synthetic aperture imaging, in which different sections of the ultrasonic imaging assembly 10 scan an image in sequence and are reassembled by the controller 56 as if the entire ultrasonic imaging assembly 10 were used at once.

Figure 9:
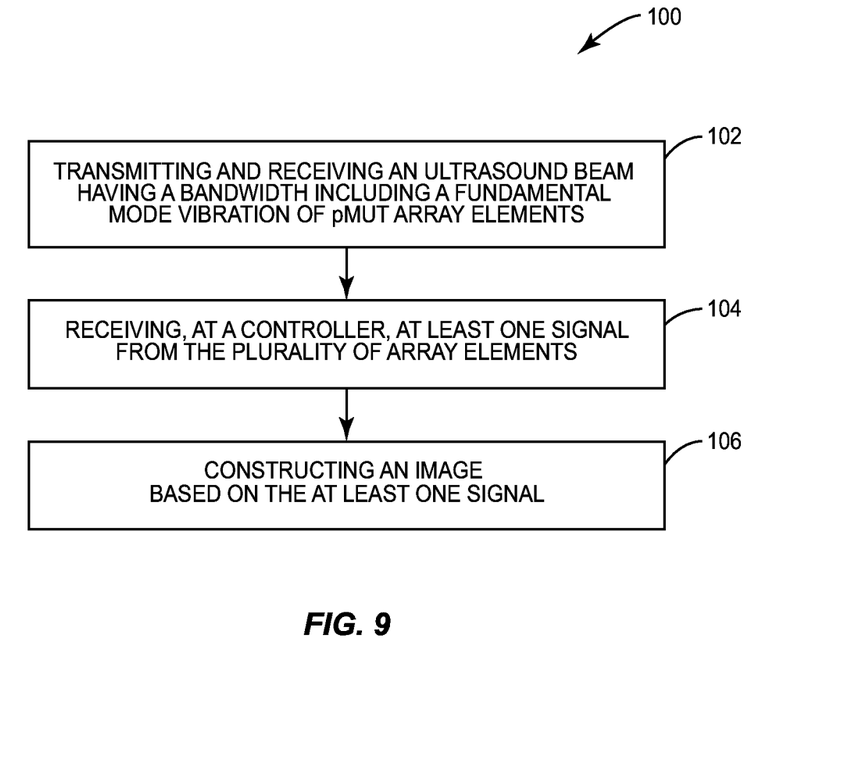
FIG. 9 is a flowchart diagram of an exemplary method of imaging a portion of an object using a pMUT ultrasound imaging array.

FIG. 9 is a flowchart diagram of an exemplary method 100 of imaging a portion of an object using a pMUT ultrasound imaging array. The method comprises transmitting and receiving, with respect to an object, an ultrasound beam having a bandwidth including a fundamental mode vibration of each of at least one Piezoelectric Micromachined Ultrasound Transducer (pMUT) of a plurality of array elements, such as the array 10 of FIG. 1. (Block 102).

The method further comprises receiving, at a controller, at least one signal from the plurality of array elements based on transmitting and receiving the at least one ultrasound beam. (Block 104). The method further comprises constructing an image of at least a portion of the object based on the at least one signal. (Block 106).

Many modifications and other embodiments of the embodiments set forth herein will come to mind to one skilled in the art to which the embodiments pertain having the benefit of the teachings presented in the foregoing descriptions and the associated drawings. Therefore, it is to be understood that the description and claims are not to be limited to the specific embodiments disclosed and that modifications and other embodiments are intended to be included within the scope of the appended claims. It is intended that the embodiments cover the modifications and variations of the embodiments provided they come within the scope of the appended claims and their equivalents. Although specific terms are employed herein, they are used in a generic and descriptive sense only and not for purposes of limitation.

We claim:

1. An ultrasonic imaging assembly comprising:
   a substrate; and
   a plurality of Piezoelectric Micromachined Ultrasound Transducer (pMUT) array elements arranged on the substrate in an array, each pMUT array element having a predetermined geometry configured to accept a predetermined fundamental mode vibration, each pMUT array element comprising:
   at least one piezoelectric layer disposed on the substrate;
   at least one first electrode connected between the at least one piezoelectric layer and a signal conductor; and
   at least one second electrode connected between the at least one piezoelectric layer and a ground conductor; and
   wherein each pMUT array element comprises a plurality of pMUTs, wherein a first group of two or more pMUTs in a first pMUT array element are connected in series between at least one signal trace and a common ground, a second group of two or more pMUTs in the first pMUT array element are connected in series between the at least one signal trace and the common ground, and the first group of two or more pMUTs and the second group of two or more pMUTs are connected in parallel between the at least one signal trace and the common ground, wherein multiple pMUT array elements of the plurality of pMUT array elements are grouped together to act as a single array element, and wherein the multiple pMUT array elements of the plurality of pMUT array elements are configured to transmit and receive ultrasound beams having a bandwidth including the predetermined fundamental mode vibration of each of the multiple pMUT array elements of the plurality of pMUT array elements, such that the single array element can transmit and receive multiple fundamental mode vibrations simultaneously.

2. The ultrasonic imaging assembly of claim 1, wherein the at least one piezoelectric layer is a lead zirconium titanate (PZT) film disposed on the substrate.

3. The ultrasonic imaging assembly of claim 1, wherein the substrate comprises a top side and a bottom side defining a first thickness,
   wherein the at least one piezoelectric layer is disposed on a first side of the substrate, and wherein the substrate comprises at least one well in a second side of the substrate, the at least one well aligned with the at least one piezoelectric layer, such that a portion of the substrate under the at least one piezoelectric layer has a second thickness less than the first thickness.

4. The ultrasonic imaging assembly of claim 1, wherein the predetermined fundamental mode vibration of each pMUT array element in the plurality of pMUT array elements is between two (2) MegaHertz (MHz) and thirty (30) MHz.

5. The ultrasonic imaging assembly of claim 1, wherein the predetermined fundamental mode vibration of at least one of the plurality of pMUT array elements is between ten (10) MegaHertz (MHz) and thirty (30) MHz.

6. The ultrasonic imaging assembly of claim 1, wherein the predetermined fundamental mode vibration of each pMUT array element in the plurality of pMUT array elements is between approximately two (2) MegaHertz (MHz) and approximately ten (10) MHz.

7. The ultrasonic imaging assembly of claim 1, wherein the predetermined fundamental mode vibration of each pMUT array element in the plurality of pMUT array elements is between ten (10) MegaHertz (Mhz) and thirty (30) MHz.

8. The ultrasonic imaging assembly of claim 1, further comprising a damping material disposed adjacent at least one edge of the substrate.

9. The ultrasonic imaging assembly of claim 1, wherein the array comprises at least one row of array elements extending in a first direction.

10. The ultrasonic imaging assembly of claim 9, wherein the plurality of pMUT array elements are configured to, upon receipt of a signal from a controller, scan at least one ultrasound beam of the ultrasound beams in an azimuth arc, such that a plane defined by the scanning of the at least one ultrasound beam defines an azimuthally scanned plane that is substantially parallel to the first direction.

11. The ultrasonic imaging assembly of claim 10, wherein the at least one row of the array elements comprises a plurality of rows extending in a second direction substantially perpendicular to the first direction.

12. The ultrasonic imaging assembly of claim 11, wherein at least one of the plurality of rows of the array elements is configured to, upon receipt of a signal from a controller, focus the at least one ultrasound beam.

13. The ultrasonic imaging assembly of claim 11, wherein at least one of the plurality of rows of the array elements is configured to, upon receipt of a signal from a controller, steer the at least one ultrasound beam in an elevation arc substantially parallel to the second direction and substantially perpendicular to the first direction and to the azimuth arc.

14. The ultrasonic imaging assembly of claim 1, wherein the plurality of pMUT array elements are configured to transmit and receive at least one ultrasound beam via pulse-echo imaging.

15. The ultrasonic imaging assembly of claim 1, wherein each pMUT array element is connected to the common ground.

16. The ultrasonic imaging assembly of claim 1, wherein the plurality of pMUT array elements comprises a plurality of groups of pMUT array elements, each group of pMUT array elements being connected to a unique ground.

17. The ultrasonic imaging assembly of claim 1, wherein at least one trench is etched into the substrate between adjacent pMUT array elements.

18. The ultrasonic imaging assembly of claim 1, wherein at least two of the multiple pMUT array elements have a different size and a different fundamental mode frequency.

19. An ultrasonic imaging apparatus comprising:
an ultrasonic imaging sub-assembly comprising:
a substrate; and
a plurality of Piezoelectric Micromachined Ultrasound Transducer (pMUT) array elements arranged on the substrate in an array, each pMUT array element having a predetermined geometry configured to accept a predetermined fundamental mode vibration, wherein each pMUT array element comprises a plurality of pMUTs, wherein a first group of two or more pMUTs in a first pMUT array element are connected in series between at least one signal trace and a common ground, a second group of two or more pMUTs in the first pMUT array element are connected in series between the at least one signal trace and the common ground, and the first group of two or more pMUTs and the second group of two or more pMUTs are connected in parallel between the at least one signal trace and the common ground, and wherein multiple pMUT array elements of the plurality of pMUT array elements are grouped together to act as a single array element, each pMUT array element comprising:
at least one piezoelectric layer disposed on the substrate;
at least one first electrode connected between the at least one piezoelectric layer and a signal conductor; and
at least one second electrode connected between the at least one piezoelectric layer and a ground conductor; and
a controller in communication with the at least one signal trace configured to:
direct the multiple pMUT array elements of the plurality of pMUT array elements, via the at least one signal trace, to transmit and receive, with respect to an object, ultrasound beams having a bandwidth including the predetermined fundamental mode vibration of each of the multiple pMUT array elements of the plurality of pMUT array elements, such that the single array element can transmit and receive multiple fundamental mode vibrations simultaneously;
receive at least one signal from the plurality of pMUT array elements based on transmitting and receiving at least one ultrasound beam of the ultrasound beams; and
construct at least one image of at least a portion of the object based on the at least one signal.

20. A method of imaging a portion of an object comprising:
transmitting and receiving, with respect to an object, ultrasound beams having a bandwidth including a predetermined fundamental mode vibration of each of multiple Piezoelectric Micromachined Ultrasound Transducer (pMUT) array elements of a plurality of pMUT array elements, wherein each pMUT array element comprises a plurality of pMUTs, wherein a first group of two or more pMUTs in a first pMUT array element are connected in series between at least one signal trace and a common ground, a second group of two or more pMUTs in the first pMUT array element are connected in series between the at least one signal trace and the common ground, and the first group of two or more pMUTs and the second group of two or more pMUTs are connected in parallel between the at least one signal trace and the common ground, and wherein the multiple pMUT array elements of the plurality of pMUT array elements are grouped together to act as a single array element, such that the single array element can transmit and receive multiple fundamental mode vibrations simultaneously, each pMUT array element comprising at least one piezoelectric layer disposed on a substrate, each pMUT array element having a predetermined geometry configured to accept the predetermined fundamental mode vibration;

receiving, at a controller, at least one signal from the plurality of pMUT array elements based on transmitting and receiving at least one ultrasound beam of the ultrasound beams; and constructing at least one image of at least a portion of the object based on the at least one signal.

21. The method of claim 20, wherein at least two of the multiple pMUT array elements have a different size and a different fundamental mode frequency.

\* \* \* \* \*